United States Patent [19]

Merrifield

[11] Patent Number: 4,560,676
[45] Date of Patent: Dec. 24, 1985

[54] N$^\alpha$-DESACETYLTHYMOSIN$\alpha_1$ AND PROCESS

[75] Inventor: Robert B. Merrifield, Cresskill, N.J.

[73] Assignee: The Rockefeller University, New York, N.Y.

[21] Appl. No.: 253,968

[22] Filed: Apr. 13, 1981

Related U.S. Application Data

[62] Division of Ser. No. 137,939, Apr. 7, 1980, Pat. No. 4,293,455.

[51] Int. Cl.$^4$ .............................................. A61K 37/00
[52] U.S. Cl. ..................................................... 514/12
[58] Field of Search ......................................... 514/12

[56] References Cited

U.S. PATENT DOCUMENTS 4,293,455 10/1981 Merrifield et al. ........... 260/112.5 R Primary Examiner—Delbert R. Phillips
Attorney, Agent, or Firm—Jon S. Saxe; Bernard S. Leon; George M. Gould

[57] ABSTRACT

The preparation of N$^\alpha$-desacetylthymosin$\alpha_1$ and its use as a hormonally active agent participating in the regulation, differentiation and function of thymic dependent lymphocytes (T-cells) is described.

2 Claims, No Drawings

$N^\alpha$-DESACETYLTHYMOSIN$\alpha_1$ AND PROCESS

RELATED APPLICATIONS

This application is a divisional application of U.S. patent application Ser. No. 137,939, filed Apr. 7, 1980, now U.S. Pat. No. 4,293,455.

BACKGROUND OF THE INVENTION

The isolation and biological activity of naturally occurring thymosin $\alpha_1$ is described in U.S. Pat. No. 4,079,127 (Goldstein et al.). Thymosin $\alpha_1$ is a component of thymosin fraction 5 which is a potent immunopotentiating preparation which has shown clinical effectiveness in increasing T-cell numbers and normalizing immune function in children with thymic dependent primary immunodeficiency diseases and can increase T-cell numbers in immunodepressed cancer patients. Thymosin $\alpha_1$ has been found to be 10 to 1000 times more active than fraction 5 in several in vitro and in vivo assay systems designed to measure T-cell differentiation and function.

The chemical synthesis of thymosin $\alpha_1$ by both solution phase and solid phase (using benzhydrylamine resin) synthetic procedures is described in U.S. Pat. No. 4,148,788 (Wang). Such procedures either employ intermediates containing acetylserine as the N-terminal group or are acetylated prior to removal of protective groups and cleavage from the resin.

An alternative solution phase synthesis of thymosin $\alpha_1$ is described by Birr and Stollenwerk, Angew. Chem. 18, 394 (1979) which also employs blocked N-terminus intermediates. Applicant, in a talk presented at the Fifteenth European Peptide Symposium, Gdansk, Poland in September 1978 described the use of the 9-(2-sulpho)-fluorenylmethyloxycarbonyl group as a reagent for the purification of synthetic peptides. During this talk it was indicated inter alia that the purification method was applied to preparing desacetylthymosin $\alpha_1$. No indication of any biological or other utility for this compound was stated. The Proceedings of the Fifteenth European Peptide Symposium, Edited by Siemion and Kupryszewski (Wroclaw University Press—Wroclaw, Poland) was published in June 1979 and contained a paper by applicant entitled "The 9-(2-Sulpho)fluorenylmethyloxycarbonyl Group, A New Reagent for the Purification of Synthetic Peptides", which contained the following statement:

"We have recently applied the method to synthetic des-acetyl thymosin $\alpha_1$. In this case the Sulfmoc-peptide was decomposed directly on the DEAE-cellulose column with 5% aqueous Et$_3$N and then eluted with 1M formic acid. This simple one-step procedure gave a dramatic improvement in the homogeneity of the product."

Additionally, applicant in conjunction with eight co-authors presented the Alan E. Pierce Award Lecture on Solid Phase Peptide Synthesis at the 6th American Peptide Symposium on June 20, 1979 which was published in December 1979 and which contained the following statement:

"This technique has been applied to several small neutral, acidic and basic peptides and to synthetic des-acetylthymosin $\alpha_1$, a 28-residue peptide containing several acidic and basic residues. In the latter case, the homogeneity of the peptide was dramatically improved by this simple one-step procedure (FIG. 2)."

Recently there has been an indication in the press (Wall Street Journal, Mar. 10, 1980) that a synthetic gene for thymosin $\alpha_1$ had been constructed, inserted into a plasmid, the recombinant plasmid inserted into E. coli and the cloned gene expressed to yield a material which was identified as thymosin $\alpha_1$. However, it is likely that the gene product was $N^\alpha$-desacetylthymosin $\alpha_1$. Similarly, it is believed that natural thymosin $\alpha_1$ is expressed as $N^\alpha$-desacetylthymosin $\alpha_1$ and then by post translation modification is converted to thymosin $\alpha_1$.

DESCRIPTION OF THE INVENTION

The present invention relates to $N^\alpha$-desacetylthymosin $\alpha_1$ in purified form. This compound, like thymosin $\alpha_1$ to which it is structurally related, exhibits potent immunopotentiating activity.

$N^\alpha$-desacetylthymosin $\alpha_1$ can be conveniently synthesized by any of the chemical methods, i.e., solid phase or solution phase peptide synthesis, known in the art for the preparation of thymosin $\alpha_1$ with the exception that serine is utilized instead of N-acetylserine for the amino terminal group.

In a preferred aspect of the present invention, $N^\alpha$-desacetylthymosin $\alpha_1$ is synthesized by an improved solid phase synthesis employing aminoacyl-4-(oxymethyl)phenylacetamidomethyl-resin (PAM) as the solid support. The ester linkage between the peptide and this PAM resin is known to have enhanced acid stability compared to the usual benzyl ester resin and to prevent loss of peptide chains during the synthesis. Use of this support is also known to help avoid trifluoroacetylation which has been a major terminating side reaction in solid phase peptide synthesis.

The synthesized peptide can be readily removed from the resin support by treatment with anhydrous hydrogen fluoride at reduced temperature, preferably at about 0° C. Since the sequence of $N^\alpha$-desacetylthymosin $\alpha_1$ contains no amino acid which may be susceptible to alkylation, HF cleavage of peptide-resin can be done without including anisole as a trap for carbonium ions. This preparation avoids the potentially serious irreversible side reaction involving acylation of anisole by the six glutamic acid residues.

After the HF treatment, the resin is extracted repeatedly with trifluoroacetic acid (TFA) and the trifluoroacetic acid is then removed, preferably by evaporation with an inert gas stream such as nitrogen. The residues after taking up in water and lyophilization consisted of [Lys(Tfa)$^{14,17,19,20}$]desacetylthymosin $\alpha_1$. The trifluoroacetyl groups on the side chains can be conveniently removed by treatment with an aqueous cyclic amine base, most preferably piperidine.

The resulting crude desacetylthymosin $\alpha_1$ can be purified directly using ion exchange and gel chromatography procedures well known in the art. The purified product was shown to be homogeneous by the criteria of paper electrophoresis, isoelectric focusing and thin layer chromatography.

Alternatively, the protected peptide resin can be selectively deblocked at the N-terminal serine by treatment with 50% trifluoroacetic acid and then reacted after neutralization with 5% N,N-diisopropylethylamine (DIEA) with 9-(2-sulfo)fluorenylmethyloxycarbonyl halide, preferably chloride, to yield the Sulfmoc derivative of the protected peptide resin. Treatment with HF at reduced temperature, extraction into aqueous phenol and purification by column chromatography yielded Sulfmoc [Lys(Tfa)$^{14,17,19,20}$]desacetylthymosin $\alpha_1$. The chromatography was accomplished by binding the Sulfmoc-peptide to a quaternary amine resin such as Ag 1-X2 which is commercially available, in 70% phenol in water, elution of the undesired underivatized peptides with 70% phenol, washing with ethanol, removal of the Sulfmoc group with dilute aqueous base (0.1N NaOH), washing with water and elution of the desacetyl-thymosin $\alpha_1$ with acetic acid. The aforesaid alternative purification procedures are summarized below in Scheme I.

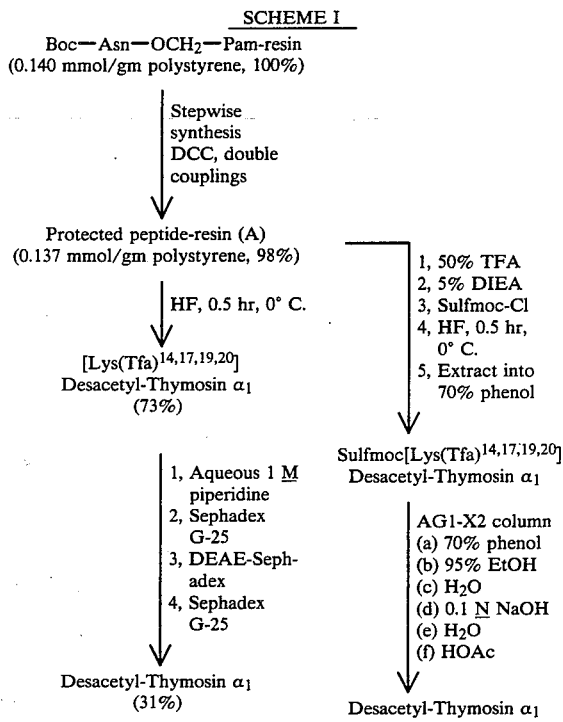

SCHEME I

In another aspect of the present invention the lysine protected desacetylthymosin $\alpha_1$ either in the form of the protected peptide resin or the protected peptide can be selectively acetylated at the amino terminal serine. Thus, for example, after the last serine residue is incorporated in the solid phase procedure, the $N^\alpha$-terminal amino group is selectively deprotected and the peptide-resin neutralized with an amine base, the resulting free amino terminus may be acetylated by treatment with a suitable acetylating agent. A preferred acetylating agent for this purpose is acetic anhydride, most preferably in the presence of pyridine. The acetylation reaction is conveniently carried out at room temperature and in an inert organic solvent, preferably a chlorinated hydrocarbon, most preferably methylene chloride. The resulting protected thymosin $\alpha_1$ resin is cleaved with HF to give [Lys(Tfa)$^{14,17,19,20}$]thymosin $\alpha_1$ and the trifluoroacetyl groups removed from lysine by treatment with an aqueous organic cyclic amine such as piperidine.

Thymosin $\alpha_1$ obtained thereby may be purified by chromatographic techniques known in the art such as, for example, by passage through a Sephadex G-25 column equilibrated in 5% acetic acid, followed by chromatography on a DEAE-Sephadex 25 column equilibrated in pH 7.4 phosphate buffer and finally desalting on a Sephadex G-25 column in 5% acetic acid.

Alternatively, the protected desacetylthymosin $\alpha_1$ resin is treated with anhydrous hydrogen fluoride as above to yield [Lys(Tfa)$^{14,17,19,20}$]desacetylthymosin $\alpha_1$. This compound can be purified via the Sulfmoc derivative (using 70% phenol for solubilization), the Sulfmoc group removed with anhydrous morpholine and the resulting compound is selectively acetylated as above at the amino terminus. The so-obtained [Lys(Tfa)$^{14,17,19,20}$]thymosin $\alpha_1$ can then be converted to thymosin $\alpha_1$ as previously described.

The peptide synthesis procedure employed in the practice of the present invention can employ any of the conventional side chain protective groups utilized in the art such as those described in U.S. Pat. No. 4,148,788 at column 6, line 31 to column 7, line 18 which disclosure is incorporated herein by reference. In preferred embodiments of this invention $N^\alpha$—Boc—amino acids are used in the synthesis whereas trifunctional amino acids are protected as $N^\alpha$—Boc—Lys(Tfa), $N^\alpha$—Boc—Thr(Bzl), $N^\alpha$—Boc—Ser(Bzl), $N^\alpha$—Boc—Asp(OBzl) and $N^\alpha$—Boc—Glu(OBzl) where Boc is tert-butyloxycarbonyl and Bzl is benzyl.

Desacetylthymosin $\alpha_1$ is a potent immunopotentiating agent and is active in the regulation, differentiation and function of T-cells. The compound of the present invention may be administered to warm blooded mammals by parenteral application either intravenously, subcutaneously or intramuscularly. Daily dosages can be provided in the range of about 0.001 to 10 mg/kg of body weight per day for intravenous administration. Obviously the required dosage will vary with the particular condition being treated, the severity of the condition and the duration of treatment. A suitable dosage form for pharmaceutical use is 1 mg. of lyophilized desacetylthymosin $\alpha_1$ to be reconstituted prior to use by the addition of sterile water or saline.

Also included in the scope of the present invention are the pharmaceutically acceptable salts of desacetylthymosin $\alpha_1$. Suitable salts include sodium, potassium or a strong organic base such as guanidine. In addition, the counter ions of these such as the chloride, bromide, sulfate, phosphate, maleate, acetate, citrate, benzoate, succinate, malate, ascorbate and the like, may be included in the preparation.

The present invention is further illustrated by the examples which follow.

EXAMPLE 1

Materials

All chemicals were reagent grade. Dichloromethane was distilled from sodium carbonate and N,N-diisopropylethylamine (DIEA) was distilled from sodium hydride. The protected amino acids are articles of commerce (Chemical Dynamics and Verga Biochemicals) and were checked for purity by thin layer chromatography (TLC). Unsubstituted resin was copoly (styrene-1% divinylbenzene) beads, 200–400 mesh (Bio-Rad). Fluorescamine (Fluram ®) was obtained from Hoffmann-La Roche Inc. PTH amino acid standards were purchased from Pierce Chemicals.

Methods

Peptide Synthesis

The syntheses of Boc—Asn-4-(oxymethyl)phenylacetic acid and of aminomethyl resin are known in the art. Boc—Asn-4-(oxymethyl)-PAM resin was prepared by coupling Boc—Asn-4-(oxymethyl)phenylacetic acid (0.492 gm., 1.30 mmole) to aminomethyl resin (3.2 gm., 0.15 mmol per gram) in the presence of dicyclohexylcarbodiimide (DCC) (0.269 gm., 1.30 mmole) in a 60 ml.

mixture of dimethylformamide (DMF)—CH$_2$Cl$_2$ (v/v, 1:2) for 21 hours. The resin was washed with CH$_2$Cl$_2$ and treated with acetic anhydride-pyridine (v/v, 1:1) for 30 minutes to acetylate any remaining amino groups. HF cleavage of the dried resin and amino acid analysis indicated a substitution of 0.140 mmol/gm. polystyrene. Amino acid analysis of resin hydrolysate (12N HCl-phenol-acetic acid, 2:1:1, v/v, 24 hours, 110° C.) also gave the same result for resin substitution.

Peptide synthesis was done with 3 gm. of substituted resin in a stepwise fashion with doubling couplings of each amino acid. All solvents were used in a ratio of 10–20 ml/gm. The protocol for a typical cycle included (i) 50% TFA—CH$_2$Cl$_2$ for 1 minute, (ii) 50% TFA—CH$_2$Cl$_2$ for 30 minutes, (iii) CH$_2$Cl$_2$ four times for 1 minute, (iv) 5% DIEA for 2 minutes, (v) CH$_2$Cl$_2$ for 1 minute, (vi) repeat steps (iv) and (v), (vii) i-propanol twice for 1 minute, (viii) CH$_2$Cl$_2$ six times for 1 minute, (ix) 3 equivalents of Boc—amino acids/CH$_2$Cl$_2$ for 5 minutes, followed by 3 equivalents of DCC for 60 minutes, (x) CH$_2$Cl$_2$ once, 2 minutes, (xi) repeat step (ix), (xii) CH$_2$Cl$_2$ six times, 2 minutes.

Coupling efficieny was monitored by the fluorescamine method (Felix and Jiminez, Anal. Biochem. 52, 377, 1973) and was judged to be >99% after two couplings for all residues monitored except for numbers 14, 17 and 22. A third coupling was performed for each of these three residues.

The following protected amino acids were then incorporated into the Asn-4-(oxymethyl)-PAM resin sequentially:

Boc—Glu(OBzl)—OH, Boc—Ala—OH, Boc—Glu(OBzl)—OH, Boc—Glu(OBzl)—OH, Boc—Val—OH, Boc—Val—OH, Boc—Glu(OBzl)—OH, Boc—Lys(Tfa)—OH, Boc—Lys(Tfa)—OH, Boc—Glu(OBzl)—OH, Boc—Lys(Tfa)—OH, Boc—Leu—OH, Boc—Asp(OBzl)—OH, Boc—Lys(Tfa)—OH, Boc—Thr(Bzl)—OH, Boc—Thr(Bzl)—OH, Boc—Ile—OH, Boc—Glu(OBzl)—OH, Boc—Ser(Bzl)—OH, Boc—Ser(Bzl)—OH, Boc—Thr(Bzl)—OH, Boc—Asp(OBzl)—OH, Boc—Val—OH, Boc—Ala—OH, Boc—Ala—OH, Boc—Asp(OBzl)—OH and Boc—Ser(Bzl)—OH.

HF Cleavage and Deprotection of Peptide

The peptide resin obtained above was treated with 10 ml. of anhydrous hydrogen fluoride (without anisole) at 0° C. At the end of thirty minutes, the hydrogen fluoride was evaporated at 0° C. and the resin was extracted three times with TFA. The trifluoroacetic acid was immediately removed by evaporation with N$_2$. The residue was suspended in water and lyophilized to give [Lys(Tfa)$^{14,17,19,20}$]desacetylthymosin $\alpha_1$ in 73% yield.

The trifluoroacetyl groups on the side chains of the four lysines were removed by treatment of either protected peptide with aqueous 1M piperidine (10 mg. protected peptide per ml.). At the end of 1 hour, the reaction mixture was neutralized with acetic acid, diluted with water and lyophilized. There was thus obtained desacetylthymosin $\alpha_1$ in crude form.

Purification of Synthetic Peptides

Part of the crude desacetylthymosin $\alpha_1$ was passed through a Sephadex G-25 column (2.6×70 cm) equilibrated in 5% acetic acid. The peptide was eluted with 5% acetic acid and lyophilized. This was followed by chromatography on a DEAE Sephadex 25 column (1×15 cm) equilibrated in pH 7.4 phosphate buffer (9.6 mM KH$_2$PO$_4$+29.7 mM K$_2$HPO$_4$) and the peptide was eluted with a 0.4M NaCl gradient in the phosphate buffer. Eluted fractions were monitored by measurement of absorbance at 570 nm aftr ninhydrin reaction of aliquots of samples. The peptide from the main peak (0.15M NaCl) was lyophilized and desalted on a Sephadex G-25 column in 5% acetic acid. The eluted fractions were pooled and lyophilized to give desacetylthymosin $\alpha_1$ as a homogeneous peptide in 31% overall isolated yield based on C-terminal Asn. Homogeneity was confirmed by paper electrophoresis R$_{Glu}$=0.14 (120 $\mu$g sample, Whatman No. 1 paper in 0.2M pyridine acetate buffer, pH 5.0, 2 hours at 1000 volts with glutamic acid as standard, paper oven-dried and sprayed with ninhydrin), isoelectric focusing pI=4.3 (200 $\mu$g sample, in 5% polyacrylamide gel at 4° C. using pH 3.5–10 ampholines (LKB) at 300 volts for 1 hour and then at 400 volts for 3 hours, the gel was stained overnight with 0.1% Coomasie Blue R-250) and TLC R$^a$=0.68 and R$^b$=0.34 (a=butanol-pyridine-acetic acid-water (30:50:10:40) and b=butanol-ethyl acetate-acetic acid-water (1:1:2:2).

Hydrolysis in 6N HCl at 110° C. for 24, 48 and 72 hours and the results were extrapolated to 0 hour for Ser and Thr to give the expected amino acid analysis (numbers in parentheses are theoretical values): Lys=4.21 (4), Asp=3.75 (4), Glu=6.29 (6), Ala=2.72 (3), Val=2.73 (3), Leu=1.00 (1), Ile=0.92 (1), Ser=2.75 (3), Thr=2.55 (3).

Solid Phase Sequencing

Sequence and preview analyses of the synthetic desacetylthymosin $\alpha_1$ were performed on a Sequemat Mini-15 Solid Phase Sequencer coupled to a Sequemat P-6 Auto Converter (Sequemat Inc., Watertown, Mass.). This was done while the peptide was still fully protected and attached to the resin. The reaction column was packed with silanized glass beads and 25 mg. of protected peptide-resin. A single column program was started by advancing to TFA treatment in order to remove the Boc group. A total of 29 cycles of degradation were carried out and the PTH-amino acids were collected in fractions. The PTH-amino acids were identified by TLC on silica GF plates (Analtech) using the solvent system chloroform-methanol (v/v, 95:5) and were visualized under short wavelength UV. Those of the aliphatic amino acids were also quantitated by high pressure liquid chromatography according to Bhown et al., J. Chromatography 148, 532 (1978).

Phenylthiohydantoins of aliphatic amino acids from the unpurified synthetic peptide-resin were compared with standard PTHs by TLC and the results indicated that those residues were correctly incorporated. Using quantitative HPLC, it was found that total previews at residues 15, 21 and 25 were 4.5%, 14.8% and 15.4%, respectively. This indicates an average of only 0.3% deletion per step for the first 15 synthetic cycles followed by an abrupt increase at one or more steps between residues 15 and 21. Between steps 21 and 27 the apparent deletion level returned to the background level. Fluorescamine monitoring data suggested that the large deletion may have occurred at Lys(Tfa)$^{17}$.

Bioassay

The desacetylthymosin $\alpha_1$ prepared and characterized above was compared with thymosin $\alpha_1$, prepared on both benzhydrylamine and PAM resins in the rosette inhibition assay (azathioprine-sensitive rosette assay) as described by Dardenne and Bach in "The Biological Action of Thymic Hormones" (van Bekkum, D. K., Ed.), page 235 (Kooyker Scientific Publications, Rotterdam, 1975). In this assay the peptides are tested for ability to restore azathioprine sensitivity in rosette formation by spleen cells of adult thymectomized mice. The two synthetic thymosin $\alpha_1$ samples and desacetylthymosin $\alpha_1$ were found to be equally active and both peptides had activity equal to that of natural thymosin $\alpha_1$. The minimum concentration required for restoration of azathioprine sensitivity was found to be between $10^{-7}$ and $10^{-8}$M for all three compounds.

EXAMPLE 2

A sample of the peptide-resin prepared in Example 1, after the last Ser residue had been incorporated, was treated with 50% TFA—$CH_2Cl_2$ to remove the Boc group. The peptide-resin was neutralized with DIEA. The amino terminus was then acetylated by treating the peptide-resin with an excess of 1:1 mixture of pyridine and [$^3$H]acetic anhydride (3.12 mCi/mmole) in $CH_2Cl_2$ for 1 hour. The acetylated peptide-resin was then washed with $CH_2Cl_2$ and dried in vacuo.

The acetylated peptide-resin (508 mg.) was treated with 10 ml. of anhydrous hydrogen fluoride without anisole at 0° C. At the end of 30 minutes, the hydrogen fluoride evaporated at 0° C. and the resin was extracted three times with TFA. The trifluoroacetic acid was immediately removed by evaporation with $N_2$. The residue was suspended in water and lyophilized to give 129 mg. of [Lys(Tfa)$^{14,17,19,20}$][$^3$H]thymosin $\alpha_1$ (77% yield by amino acid analysis).

The trifluoroacetyl groups on the side chains of the four lysines were removed by treatment with aqueous 1M piperidine (10 mg. protected peptide per ml.). At the end of 1 hour the reaction mixture was neutralized with acetic acid, diluted with water and lyophilized.

A sample (57.5 mg.) of the crude thymosin $\alpha_1$ obtained above was purified in the same manner as described in Example 1 utilizing a Sephadex G-25 column, a DEAE-Sephadex 25 column (one major peak eluted at 0.19M NaCl followed by radioactivity and/or absorbance at 570 nm after ninhydrin treatment) and desalting on a Sephadex G-25 column. The eluted fractions were pooled and lyophilized to give 22.4 mg. of thymosin $\alpha_1$ (34% overall isolated yield based on C-terminal Asn).

Tryptic digestion of a sample (1 mg.) of this purified thymosin $\alpha_1$ preparation and mapping on cellulose TLC plates gave a similar map as obtained with a sample of thymosin $\alpha_1$ synthesized previously by solid phase methods which in turn had been compared with natural thymosin $\alpha_1$. The purified thymosin $\alpha_1$ was homogeneous as shown by paper electrophoresis ($R_{Glu}=0.31$ at pH 5.0), isoelectric focusing in polyacrylamide gel (pI=4.1) and TLC ($R^a=0.68$ and $R^b=0.45$) using the same conditions for these tests as set forth in Example 1.

Amino acid analysis after hydrolysis in 6N HCl at 110° C. for 24, 48 and 72 hours and extrapolating to 0 hour for Ser and Thr gave the following values:

Lys=3.87 (4), Asp=3.92 (4), Glu=6.20 (6), Ala=2.93 (3), Val=2.77 (3), Leu=1.00 (1), Ile=0.93 (1), Ser=2.90 (3), Thr=2.70 (3).

A sample of this purified thymosin $\alpha_1$ was utilized in the bioassay comparison described in Example 1.

EXAMPLE 3

A sample of protected desacetylthymosin $\alpha_1$ resin prepared in Example 1 was treated with 50% TFA to selectivity deblock the amino terminus. After neutralization with 5% DIEA the peptide-resin was reacted with Sulfmoc-Cl to yield N-terminal Sulfmoc-peptide-resin. Treatment of this product with anhydrous hydrogen fluoride for 0.5 hour at 0° C. provided Sulfmoc[Lys(Tfa)$^{14,17,19,20}$]desacetylthymosin $\alpha_1$. Purification of this compound by chromatography over an AGI-X2 column in 70% phenol and removal of the Sulfmoc group was carried out according to the procedures set forth in Scheme I above. There was thus obtained desacetylthymosin $\alpha_1$ essentially identical to the material produced in Example 1.

EXAMPLE 4

A sample of purified Sulfmoc[Lys(Tfa)$^{14,17,19,20}$]desacetylthymosin $\alpha_1$ prepared by the procedure of Example 3 is treated with anhydrous morpholine to produce [Lys(Tfa)$^{14,17,19,20}$]desacetylthymosin $\alpha_1$. Treatment of this selectively protected compound with acetic anhydride pyridine in analogy to the acetylation procedure described in Example 2 and the resulting [Lys(Tfa)$^{14,17,19,20}$]thymosin $\alpha_1$ is deprotected and purified to homogenity following the procedures of said Example 2.

I claim:
1. Desacetylthymosin $\alpha_1$ as a homogeneous peptide.
2. A pharmaceutical dosage form comprising a minor, immunopotentiating amount of desacetylthymosin $\alpha_1$ and a major amount of a conventional parenteral carrier material.

* * * * *